(12) United States Patent
Coutard et al.

(10) Patent No.: US 11,639,893 B2
(45) Date of Patent: May 2, 2023

(54) DEVICE FOR OBSERVING A BIOLOGICAL SAMPLE IN THE INFRARED RANGE

(71) Applicant: COMMISSARIAT A L'ENERGIE ATOMIQUE ET AUX ENERGIES ALTERNATIVES, Paris (FR)

(72) Inventors: Jean-Guillaume Coutard, Grenoble (FR); Cedric Allier, Grenoble (FR); Sebastien Becker, Grenoble (FR); Mathieu Dupoy, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 17/678,714

(22) Filed: Feb. 23, 2022

(65) Prior Publication Data

US 2022/0178820 A1 Jun. 9, 2022

Related U.S. Application Data

(63) Continuation of application No. 17/268,250, filed as application No. PCT/FR2019/051904 on Aug. 5, 2019, now Pat. No. 11,313,792.

(30) Foreign Application Priority Data

Aug. 14, 2018 (FR) .................................. 18 57483

(51) Int. Cl.
  *G01N 21/35* (2014.01)
  *G01N 21/3563* (2014.01)
  (Continued)

(52) U.S. Cl.
  CPC ......... *G01N 21/3563* (2013.01); *G01N 21/39* (2013.01); *G01N 33/4833* (2013.01); *G01N 2201/06113* (2013.01)

(58) Field of Classification Search
  CPC .............. G01N 21/3563; G01N 21/39; G01N 33/4833; G01N 2201/06113
  See application file for complete search history.

(56) References Cited

U.S. PATENT DOCUMENTS

2002/0018199 A1  2/2002  Blumenfeld et al.
2012/0122084 A1  5/2012  Wagner et al.
(Continued)

FOREIGN PATENT DOCUMENTS

FR  3 034 197 A1  9/2016

OTHER PUBLICATIONS

International Search Report dated Dec. 13, 2019 in PCT/FR2019/051904, 3 pages.
(Continued)

*Primary Examiner* — Hugh Maupin
(74) *Attorney, Agent, or Firm* — Oblon, McClelland, Maier & Neustadt, L.L.P.

(57) ABSTRACT

A device for observing a biological sample is provided, including: a light source to emit a light beam at a wavelength between 1 μm and 20 μm; an image sensor including pixels defining a detection plane; a holder to hold the sample between the source and the sensor at a distance from the plane smaller than 1 mm, such that the source is configured to illuminate an area of the sample larger than 1 mm², no image-forming optics are placed between the sample and the sensor, and the sensor is configured to acquire an image corresponding to an area of the sample larger than 1 mm² and representative of an absorption of the beam by the sample at the wavelength; and a processor to determine a map of an amount of analyte in the sample, based on the image acquired by the sensor, the analyte absorbing light at the wavelength.

10 Claims, 4 Drawing Sheets

(51) Int. Cl.
  *G01N 21/39*   (2006.01)
  *G01N 33/483*  (2006.01)

(56) References Cited

U.S. PATENT DOCUMENTS

| | | | |
|---|---|---|---|
| 2013/0258091 A1* | 10/2013 | Ozcan | G06V 20/69 |
| | | | 348/79 |
| 2017/0220000 A1 | 8/2017 | Ozcan et al. | |
| 2018/0113064 A1 | 4/2018 | Allier et al. | |
| 2019/0137932 A1 | 5/2019 | Ozcan et al. | |
| 2019/0294108 A1 | 9/2019 | Ozcan et al. | |
| 2021/0209337 A1* | 7/2021 | Ozcan | H04N 5/2256 |

OTHER PUBLICATIONS

Dirk Lange et al., "A Microfluidic Shadow Imaging System for the Study of the Nematode *Caenorhabditis elegans* in Space", Sensors and Actuators B, vol. 107, No. 2, XP027810555, Jun. 29, 2005, pp. 904-914.

Richards PL., "Bolometers for Infrared and Millimeter Waves" Journal of Applied Physics., vol. 76, No. 1, XP000459427, Jul. 1, 1994, pp. 1-24.

Hemmel Amrania et al., "Digistain: a digital staining instrument for histopathology", Optics Express, vol. 20, No. 7, Mar. 26, 2012, pp. 7290-7299.

\* cited by examiner

DEVICE FOR OBSERVING A BIOLOGICAL SAMPLE IN THE INFRARED RANGE

CROSS-REFERENCE TO RELATED APPLICATIONS

This application is a continuation of and claims benefit under 35 U.S.C. § 120 to U.S. patent application Ser. No. 17/268,250, filed Feb. 12, 2021, which is a U.S. national stage application of PCT/FR2019/051904, filed Aug. 5, 2019, and claims the benefit of priority under 35 U.S.C. § 119 to FR 18 57483 filed Aug. 14, 2018, the entire contents of each of which are incorporated herein by reference.

TECHNICAL FIELD

The technical field of the invention is related to the observation of a sample, in particular a biological sample, the observation being made for the purposes of histological analysis. The sample is observed in a lensless imaging configuration.

BACKGROUND

The characterization of biological samples by infrared spectral imaging is now a technology that has been widely described in the literature with respect to its applications in diagnostics, and in particular in the field of histopathology. It allows, without labeling, biomolecular information relating to cells or tissues to be obtained. This method is based on a spectral signature of a sample with respect to a pathology. When a light beam passing through the sample has a wavelength corresponding to an energy between two molecular vibrational levels, some of the beam is absorbed. Thus, by absorption spectrometry, it is possible to estimate a spectral absorbance of the sample, allowing information on the molecular composition of the latter to be obtained. The absorbance spectrum therefore forms a molecular signature of the sample.

However, in this type of method, it is necessary to scan the sample with a laser beam. Specifically, the spatial resolution of the measurement is dependent on the size of the laser beam. Thus, when it is desired to obtain spatially resolved spectral information, the laser beam must be narrow. As a result, it takes a long time to analyze an area of sample of a few mm$^2$ or a few cm$^2$. In addition, the instrumentation associated with infrared spectral imaging is complex and expensive.

Document US2012/0122084A1 describes a device for characterizing cells, by measuring an absorption, in the infrared domain, using an infrared photodetector. A visible image sensor allows the cell to be located, or its orientation to be determined.

Excluding the infrared domain, the observation of samples, and in particular biological samples, by lensless imaging has undergone significant advances in the last ten years. This technique allows a sample to be observed by positioning it between a light source and an image sensor, without positioning an image-forming lens between the sample and the image sensor. Thus, the image sensor collects an image of a light wave transmitted by the sample, without conjugation between the image sensor and the sample.

Document WO2008090330 for example describes a device allowing biological particles to be observed by lensless imaging. The biological particles are for example cells. The device allows an interference pattern to be associated with each cell, the morphology of the interference pattern allowing the type of cell to be identified. Lensless imaging thus appears to be a simple and inexpensive alternative to a conventional microscope. In addition, it provides a field of observation that is clearly much larger than it is possible for that of a microscope to be.

In the visible domain, lensless imaging has been applied to examine tissue slides, such as pathology slides. Examples of application have for example been described in WO2016189257 or in EP3199941. Usable images of the sample are thus obtained, but these images do not contain molecular information, or information on the type of cells present in the sample.

In the infrared domain, an application of lensless imaging is presented in EP3147646. In this document, a method allowing an image of a particle to be formed is described. The obtained image allows a particle to be observed.

Another approach to lensless imaging is described in US20050190286. In this document, formation of an image of particles deposited in contact with pixels of an image sensor is described. This method may be referred to as a shadowgraph method. The image formed by the image sensor comprises shadows of each particle, this allowing the shape of each particle to be determined. It is then possible to identify the particles depending on their shape.

The inventors propose a method allowing a sample, in particular a tissue slide, to be characterized using a relatively simple device. The method allows a large field of observation to be addressed, allowing a result to be obtained rapidly. It allows a map of the sample to be obtained, with a view to determining information regarding molecules or molecular bonds. The map produced may be used to establish a diagnosis.

SUMMARY

One subject of the invention is a method for observing a sample, notably a biological sample, the sample being placed between a light source and a pixelated image sensor, the light source emitting an incident light beam, which propagates to the sample along a propagation axis, and at an emission wavelength comprised between 1 μm and 20 μm, the method comprising the following steps:

a) illuminating the sample with the light source;
b) acquiring an image of the sample with the pixelated image sensor, no image-forming optic being placed between the sample and the image sensor; the method being characterized in that the sample is able to absorb some of the incident light beam, such that the acquired image is representative of an absorption of the incident beam by the sample, at the emission wavelength.

Preferably, the emission wavelength is comprised between 5 μm and 20 μm. Preferably, the light source is a laser light source.

According to one embodiment, the method also comprises the following steps:

c) illuminating the image sensor with the light source, at the emission wavelength, with no sample between the image sensor and the light source, so as to obtain a background image;
d) comparing the image acquired in step b) and the background image acquired in step c) to obtain an image of the absorbance of the sample at the emission wavelength.

The comparison may notably take the form of a ratio.

According to one embodiment, the emission wavelength is an absorption wavelength of an analyte, corresponding to an absorption peak of the analyte, the method comprising mapping an amount of the analyte in the sample on the basis of the image of the absorbance at the emission wavelength. By absorption peak of an analyte, what is meant is a wavelength range corresponding to a local absorption maximum.

According to one embodiment, the emission wavelength is an absorption wavelength of an analyte, corresponding to an absorption peak of the analyte, so as to obtain an image of the absorbance of the sample at the absorption wavelength, the method comprising the following steps:

e) illuminating the sample at a base wavelength, at which the absorption of the analyte is lower than the absorption of the analyte at the absorption wavelength;

f) acquiring an image of the sample with the pixelated image sensor;

g) illuminating the image sensor with the light source, at the base wavelength, with no sample between the image sensor and the light source, so as to obtain a background image at the base wavelength;

h) comparing the image acquired in step f) and the background image acquired in step g) to obtain an image of the absorbance of the sample at the base wavelength.

By absorption of the analyte, what is meant is an absorption of the incident light beam by the analyte.

The base wavelength is preferably a wavelength close to the absorption peak of the analyte. It may notably be a wavelength defining a baseline of the absorption peak.

The method may then comprise subtracting the absorbance images of the sample at the absorption wavelength and at the base wavelength, respectively, so as to obtain an image of absorbance due to the analyte.

According to one embodiment, steps a) to d) are repeated so as to successively illuminate the sample at:
a first absorption wavelength, corresponding to an absorption wavelength of a first analyte;
a second absorption wavelength, corresponding to an absorption wavelength of a second analyte;
so as to obtain images of the absorbance of the sample at the first absorption wavelength and at the second absorption wavelength, respectively.

Steps e) to h) may also be repeated so as to successively illuminate the sample at:
a first base wavelength, at which the absorption of the first analyte is lower than the absorption of the first analyte at the first absorption wavelength ($\lambda_{a,1}$);
a second base wavelength, at which the absorption of the second analyte is lower than the absorption of the second analyte at the second absorption wavelength;
so as to obtain images of the absorbance of the sample at the first base wavelength and at the second base wavelength, respectively.

The method may also comprise:
subtracting the images of absorbance of the sample at the first absorption wavelength and at the first base wavelength, respectively, so as to obtain an image of absorbance due to the first analyte;
subtracting the images of absorbance of the sample at the second absorption wavelength and at the second base wavelength, respectively, so as to obtain an image of absorbance due to the second analyte;
comparing the image of absorbance due to the first analyte and the image of absorbance due to the second analyte.

The method may comprise one of the following features, implemented alone or in any technically achievable combination:
the sample is a slide of biological tissue;
the light source illuminates an area of the sample larger than 1 mm$^2$ or larger than 5 mm$^2$;
the image acquired of the sample by the image sensor corresponds to an area of sample larger than 1 mm$^2$ or larger than 5 mm$^2$;
the pixels of the image sensor define a detection plane, the sample being placed at a distance from the detection plane smaller than 1 mm;
the method comprises, on the basis of the acquired image, a step of determining at least one region of interest of the sample.

The sample may be held by a carrier comprising at least one of the following materials:
silicon;
and/or germanium;
and/or calcium fluoride;
and/or barium fluoride.

Another subject of the invention is a device for observing a sample, comprising a light source emitting in a spectral band comprised between 1 μm and 20 μm, an image sensor sensitive in said spectral band, and an element for holding the sample and suitable for receiving a sample, the sample-holding element being configured such that the sample, when it is placed on the holding element, lies between a light source and an image sensor, the device being such that no image-forming optic is placed between the sample, when it is placed on the sample-holding element, and the image sensor. The device may comprise a processing unit, a microprocessor for example, configured to receive at least one image acquired by the image sensor, and to implement the image-processing operations described above or below.

Other advantages and features will become more clearly apparent from the following description of particular embodiments of the invention, which are provided by way of nonlimiting examples, and which are shown in the figures listed below.

BRIEF DESCRIPTION OF THE FIGURES

FIG. 2B is representative of an absorption of the first sample at a wavelength of 7.35 μm.

DETAILED DESCRIPTION OF EMBODIMENTS

Figure 1:
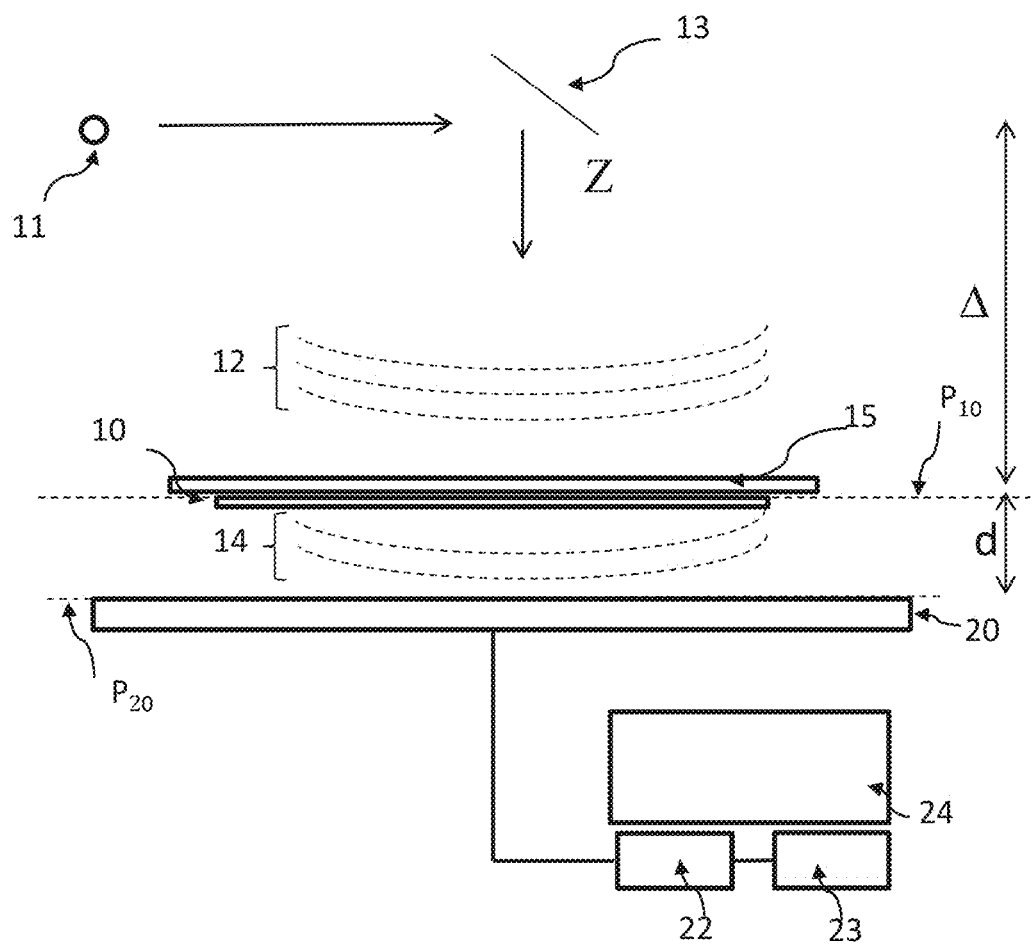
FIG. 1 shows a device allowing the invention to be implemented.

FIG. 1 shows an example of a device allowing the invention to be implemented. A light source 11 is configured to emit a light beam 12, called the incident light beam, that propagates in the direction of a sample 10. The incident light beam reaches the sample by propagating along a propagation axis Z.

In this example, the sample 10 is a biological sample that it is desired to characterize. It may notably be a tissue slide intended for histological analysis, or pathology slide, comprising a small thickness of tissue deposited on a transparent slide 15 that acts as a sample carrier. By small thickness, what is meant is a thickness preferably smaller than 100 μm, and preferably smaller than 10 μm, typically of a few microns. The sample lies in a plane $P_{10}$, called the sample plane. The sample plane is preferably perpendicular or substantially perpendicular to the propagation axis Z. The term substantially perpendicular means perpendicular to within an angular tolerance of a few degrees, smaller than 20° or 10°.

The tissue slide 10 is obtained according to known preparation methods, from a tissue sample extracted by biopsy or a swab. The sample is then prepared so as to be in the form of a small thickness deposited on the transparent slide 15. Such methods are known in the field of histology. They for example comprise a slice of frozen tissue, or sampled tissue embedded in a paraffin-wax matrix. Preferably, the sample has not been labeled beforehand, by means of an exogenous marker added to the sample before its analysis.

The sample may comprise an analyte, a spatial distribution of which in the sample it is desired to evaluate. By analyte, what is meant is, for example, a molecule or a portion of a molecule or a molecular bond.

The slide 15 is transparent to the incident beam 12. It may comprise or consist of materials such as silicon, germanium, calcium fluoride ($CaF_2$) and barium fluoride ($BaF_2$).

The distance A between the light source and the sample, along the axis Z, is preferably larger than 1 cm. It is preferably comprised between 2 and 30 cm. Preferably, the light source, seen by the sample, is considered to be point-like. This means that its diameter (or its diagonal) is preferably smaller than one tenth, and better still one hundredth, of the distance between the sample and the light source. Thus, the light preferably reaches the sample in the form of plane waves, or waves that may be considered as such.

The light source 11 is a source that emits in the infrared. It may be a question of the short wavelength infrared (SWIR), which lies between 1 and 3 μm, or of the medium wavelength infrared (MWIR), which lies between 3 and 5 μm, or even of the long wavelength infrared (LWIR), which lies between 8 and 20 μm. Thus, generally, the incident beam 12 is emitted at a wavelength λ lying between 1 μm and 20 μm, this corresponding to a wavenumber (1/λ) comprised between 500 $cm^{-1}$ and 10000 $cm^{-1}$. In the example shown, the device comprises a reflector 13, for reflecting the light beam 12 emitted by the light source 11 toward the sample. Preferably, the wavelength is comprised between 5 μm and 20 μm.

The light source 11 is preferably a laser source. It may notably be a laser source the wavelength of which is tunable, such as for example a quantum cascade laser (QCL), and in particular an external-cavity laser. The width of the emission spectral band of the light source is preferably smaller than 50 nm, or even than 10 nm, or even than 5 nm. A light source may comprise a plurality of elementary QCL laser sources, respectively emitting in various spectral bands.

The sample 10 is placed between the light source 11 and an image sensor 20. The latter preferably lies parallel, or substantially parallel, to the transparent slide 15 carrying the sample. The term "substantially parallel" means that the two elements may not be rigorously parallel, an angular tolerance of a few degrees, smaller than 20° or 10°, being acceptable. The sample is placed on a holding element, configured to hold the sample, and its carrier, between the light source and the image sensor.

Under the effect of illumination by the light beam 12, propagating along the propagation axis Z to the sample, the latter transmits a light wave 14, called the transmitted light wave. The transmitted light wave 14 propagates, parallel to the axis Z, to an image sensor 20. The sample absorbs some of the light beam 12. Thus, the transmitted light wave 14 corresponds to a portion of the light beam 12 not absorbed by the sample.

The image sensor 20 is able to form an image of the transmitted light wave 14 in a detection plane $P_{20}$. In this example, the image sensor is formed by a matrix-array of bolometers, each bolometer of the matrix-array having a detection spectral band comprised between 5 μm and 20 μm. Each bolometer forms a pixel. In the examples described below, each pixel is formed by one vacuum-encapsulated bolometer. Conventionally, a dark image, corresponding to the noise of each bolometer in the absence of illumination, may be acquired. The dark image is then subtracted from each acquired image. When the sample is placed between the image sensor and the light source, the image acquired by the image sensor is representative of the absorption of the incident beam 12 by the sample 10.

When the image sensor 20 comprises non-functional pixels, or dead pixels, the intensity of each non-functional pixel is replaced by an average of the intensities measured by the pixels adjacent to the non-functional pixel.

The distanced between each pixel and the sample 10 is preferably smaller than 5 mm. The smaller it is, the better the spatial resolution of the image acquired by the image sensor. Also, it is advantageous for the distance d to be smaller than 1 mm, or even smaller than 500 μm. The sample may be deposited in direct contact with the pixels of the image sensor 20, in a shadowgraph configuration such as described in US20050190286.

Due to the absence of image-forming optic between the sample 10 and the image sensor 20, the field of observation of the image sensor is defined by the size of the image sensor and the size of the incident beam. The field of observation may be larger than 1 $mm^2$, or even larger than 5 $mm^2$ or 10 $mm^2$. Therefore, the acquisition of a single image allows an intensity of the light wave 14 transmitted by several $mm^2$ of the sample, typically at least 5 or 10 $mm^2$ of the sample, to be obtained simultaneously.

Preferably, the transparent slide 15 comprises an anti-reflective coating. For example, when the transparent slide is made of silicon, it may comprise a thin layer of germanium or of zinc sulfide (ZnS). This allows the appearance of interference fringes in the images formed by the image sensor to be limited. In the absence of a thin anti-reflective layer, the transparent slide 15 behaves like a Fabry-Perot cavity, this leading to the formation of undesirable interference fringes in the image acquired by the image sensor 20.

A processing unit, for example taking the form of a microprocessor 22, is configured to perform, on the basis of the images acquired by the image sensor 20, image-processing operations such as described below. The microprocessor 22 is connected to a memory 23, which contains instructions relating to the image-processing operations to be carried out. It may be connected to a screen 24.

Figure 2A:
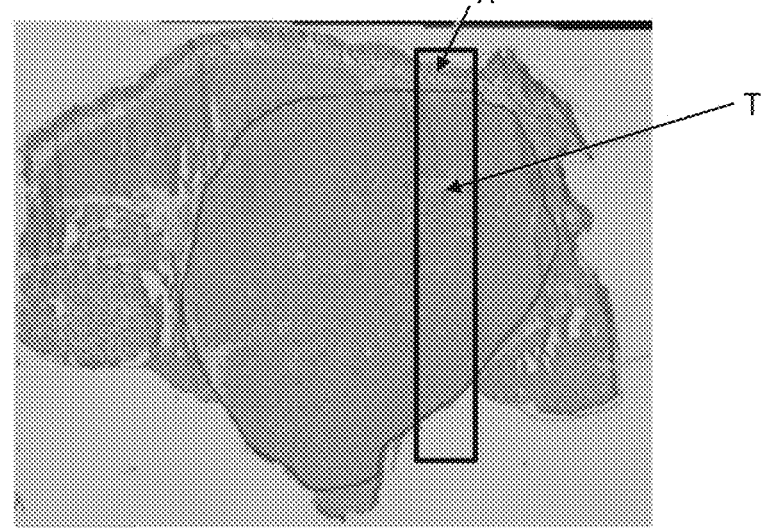
FIG. 2A is a visible image of a first sample.

FIG. 2A shows a first sample that was examined using a device such as illustrated in FIG. 1. It is a question of a section of muscle tissue taken from a mouse and then frozen. The sampled tissue contained a tumor as a result of injection of CAL33 tumor cells. It was sliced to obtain a sample of thickness equal to 4 μm. The sample was then deposited on a silicon slide or on a slide of $CaF_2$ (calcium fluoride).

The experimental set-up was:
light source: QCL laser source emitting at the wavelength of 7.35 μm;
diameter of the incident beam: 1.5 mm;

image sensor: matrix-array of 80×80 bolometers of 17 μm side length, with a center-to-center distance between each pixel equal to 30 μm, giving a field of observation of about 2.4×2.4 mm².

Figure 2B:
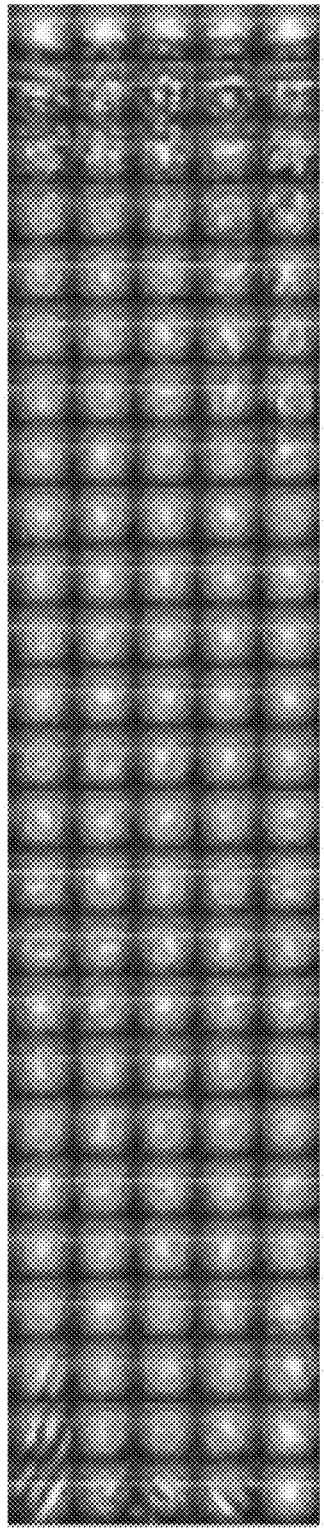
FIG. 2B shows images of the first sample, obtained by implementing the invention.

The slide 15 was mounted on a translation stage, so as to be translated in two orthogonal directions X and Y perpendicular to the propagation axis Z. A scan allowed a matrix-array of 150 images arranged in 25 rows and 6 columns to be obtained. The field covered by the matrix-array of images corresponds to a sample area 3 mm wide and 12.5 mm long. The observed area of the sample has been framed by a box in FIG. 2A. The central region of the sample, designated by the letter T, corresponds to a malignant tumor whereas the peripheral region, designated by the letter H, corresponds to healthy tissue. FIG. 2B shows the images acquired by the image sensor.

It may be seen that the images corresponding to the cancerous region T have a dense appearance, whereas the images corresponding to the healthy region H have a spongy appearance. Thus, an infrared image, acquired using a lensless imaging method, allows the presence of a cancerous region to be detected and viewed. It allows a region of interest corresponding to the cancerous region or to the healthy region to be defined in the sample.

FIGS. 3A to 3D correspond to a second embodiment, in which a plurality of images of a sample are produced, by modulating the wavelength λ of the illumination beam 12.

It is known that the spectral light transmittance of a sample varies as a function of the composition of the latter, because of the presence of absorption peaks corresponding to modes of vibration of the molecules from which the sample is composed. The presence of absorption peaks is the basis of vibrational spectrometry methods such as infrared spectroscopy or Raman spectrometry.

By transmittance $tr_{\lambda_i}$, what is meant is a ratio between an intensity $i_{\lambda_i}$ of the light wave 14 transmitted by the sample, and detected by the image sensor, at the wavelength $\lambda_i$, to an intensity of the light wave detected by the image sensor, at the same wavelength, in the absence of a sample.

Thus, according to the Beer-Lambert law:

$$tr_{\lambda_i} = \frac{i_{\lambda_i}}{i_{0,\lambda_i}} \quad (1)$$

where $i_{0,\lambda_i}$ is the intensity detected by the image sensor in the absence of a sample.

The absorbance $abs_{\lambda_i}$ at the wavelength $\lambda_i$ is obtained using the expression:

$$abs_{\lambda_i} = -\ln(tr_{\lambda_i}) = -\ln\left(\frac{i_{\lambda_i}}{i_{0,\lambda_i}}\right). \quad (1')$$

Figure 3A:
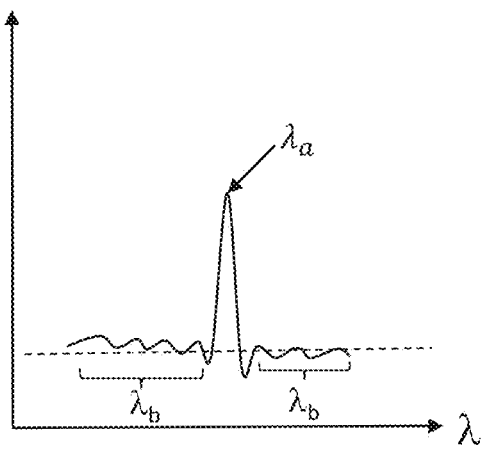
FIG. 3A schematically shows an absorption peak of an analyte.

FIG. 3A shows an example of the absorption spectrum of an analyte, the x-axis representing the wavelength. An absorption peak, indicated by an arrow, at an absorption wavelength $\lambda_a$ may be seen. On either side of the absorption peak lies a baseline, identified by a dashed line. The baseline corresponds to base wavelengths $\lambda_b$, lying on either side of the absorption peak. Thus, a base wavelength is a wavelength located outside the absorption peak of the analyte. Preferably, a base wavelength bounds the absorption peak. At the base wavelength, the absorption of the incident light beam by the analyte is lower than the absorption of the incident beam by the analyte in the absorption peak.

The approach proposed by the inventors consists in determining a map of an absorbance resulting from the presence of an analyte, the absorption wavelength $\lambda_a$ of which is known. To do this, the method consists in:

acquiring an image, representative of the absorption of the light beam 12 by the sample, corresponding to an image $I_{\lambda_a}$ acquired by the image sensor when the illumination beam is emitted at the absorption wavelength $\lambda_a$ of the analyte. Such an image is designated by the term "absorption image".

acquiring an image, called the background image, corresponding to an image $I_{0,\lambda_a}$ acquired by the image sensor in the absence of a sample, at the absorption wavelength $\lambda_a$.

Comparison of the absorption image $I_{\lambda_a}$ and background image $I_{0,\lambda_a}$ may make it possible to obtain an absorbance image $Abs_a$, of the sample, at the absorption wavelength $\lambda_a$, such that:

$$Abs_{\lambda_a}(x, y) = -\ln\left(\frac{I_{\lambda_a}(x, y)}{I_{0,\lambda_a}(x, y)}\right) \quad (2)$$

where $Abs_{\lambda_a}(x,y)$ is the value of the absorbance image $Abs_{\lambda_a}$ at the coordinates (x,y);

$I_{\lambda_a}(x,y)$ and $I_{0,\lambda_a}(x,y)$ are the intensities of the pixels of the absorption and background image at the coordinate (x,y), respectively. These images may be corrected using the dark image of the image sensor.

The coordinates (x,y) are defined in the detection plane $P_{20}$. Since the latter is parallel to the sample plane $P_{10}$, the coordinates (x,y) also correspond to coordinates in the sample plane $P_{10}$.

On the basis of the absorbance image $Abs_{\lambda_a}$, it is possible to estimate an amount Q(x,y) of analyte at each coordinate (x,y), with $$Q(x, y) = -\frac{Abs_{\lambda_a}(x, y)}{\mu_{\lambda_a}\varepsilon(x, y)}, \quad (3)$$

where $\varepsilon(x,y)$ is the thickness of the sample, along the propagation axis Z, at the coordinates (x,y);

$\mu_{\lambda_a}$ is the absorption coefficient of the analyte, per unit length, at the wavelength $\lambda_a$.

Figure 3B:
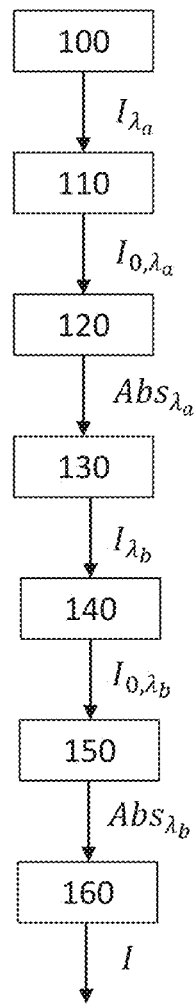
FIG. 3B contains the main steps of one embodiment of the invention.

These steps are summarized in FIG. 3B:

Step 100: acquiring an absorption image $I_{\lambda_a}$, when the sample is illuminated by a light source at the absorption wavelength $\lambda_a$.

Step 110: acquiring a background image $I_{0,\lambda_a}$, with no sample between the image sensor and the light source, at the absorption wavelength $\lambda_a$.

Step 120: computing a ratio between the absorption image and the background image, to obtain an absorbance image of the sample $Abs_{\lambda_a}$, at the absorption wavelength $\lambda_a$.

According to one variant, the sample is illuminated at a base wavelength $\lambda_b$, at which the absorption of the incident beam by the sample is lower than the absorption at the absorption wavelength $\lambda_a$. The method then comprises the following steps:

Step 130: acquiring an absorption image $I_{\lambda_b}$, when the sample is illuminated by a light source at the base wavelength $\lambda_b$.

Step 140: acquiring a background image $I_{0,\lambda_b}$, with no sample between the image sensor and the light source, at the base wavelength $\lambda_b$.

Step 150: computing a ratio between the absorption image and the background image, to obtain an absorbance image of the sample $Abs_{\lambda_b}$, at the base wavelength $\lambda_b$.

Step 160: subtracting the absorbance image of the sample at the base wavelength from the absorbance image of the sample at the absorption wavelength, so as to obtain an image I, representative of the absorbance due to the analyte.

$$I = Abs_{\lambda_a} - Abs_{\lambda_b}.$$

However, it may be difficult to estimate amounts of analyte quantitatively. The inventors believe that it may be preferable to perform comparisons between absorbance images resulting from various analytes, and for example from various biomarkers.

It is known that cancerous activity may be characterized by a morphological indicator, representative of a ratio between the volume of the nucleus and the volume of the cytoplasm in the sample. Specifically, it is known that cancer cells have a higher metabolic activity than healthy cells. Thus, they tend to have a nucleus the volume of which is larger than that of healthy cells. Therefore, the ratio of nuclear volume to cytoplasm volume is an indicator used by histopathologists to establish the malignancy of a tumor.

The publication Amrania H "Digistain: a digital staining instrument for histopathology", Optics Express 7299, Vol. 20, No. 7, 26 Mar. 2012, describes a method based on a comparison of the absorbance due to $PO_2^-$ groups, representative of phosphodiester bonds inside the cell nucleus, and of the absorbance due to Amide bonds, the latter being representative of peptide bonds, inside the cytoplasm. By making a comparison between the absorbance due to phosphodiester bonds and the absorbance due to peptide bonds, a morphological indicator representing a nuclear volume/cytoplasmic volume ratio may be obtained.

The inventors were inspired by this method. Specifically, they successively illuminated a sample, such as described with reference to FIG. 2A, at various wavelengths $\lambda_{a,1}, \lambda_{a,2}, \lambda_{b,1}$ and $\lambda_{b,2}$, such that:
- $1/\lambda_{a,1} = 1081$ cm$^{-1}$, which corresponds to an absorption peak of $PO_2^-$;
- $1/\lambda_{a,2} = 1654$ cm$^{-1}$, which corresponds to an absorption peak of an Amide group, in a spectral band commonly referred to as Amide I, which corresponds to a vibration of the C=O bond.
- $1/\lambda_{b,1} = 951$ cm$^{-1}$, which corresponds to the baseline about the absorption peak of $PO_2^-$;
- $1/\lambda_{a,2} = 1491$ cm$^{-1}$, which corresponds to the baseline about the Amide I absorption peak.

The light source used included 4 QCL lasers, respectively emitting in the following spectral ranges:
- 1949 cm$^{-1}$ to 1706 cm$^{-1}$;
- 1712 cm$^{-1}$ to 1410 cm$^{-1}$;
- 1464 cm$^{-1}$ to 1149 cm$^{-1}$;
- 1218 cm$^{-1}$ to 896 cm$^{-1}$.

At each wavelength $\lambda$, two images were acquired:
- a background image $I_{0,\lambda}$, with no sample between the light source and the image sensor;
- an image of absorption $I_\lambda$, the sample being placed between the light source and the image sensor.

By calculating a ratio between the absorption image $I_\lambda$ and the background image $I_{0,\lambda}$, absorbance images $Abs_\lambda$ were obtained at each wavelength $\lambda$.

Thus, for each analyte, in this case for $PO_2^-$ and the Amide bond, the following were obtained:
- an image of absorbance in each absorption peak; these images being denoted $Abs_{\lambda_{a,1}}$ and $Abs_{\lambda_{a,2}}$;
- an image of absorbance at the baseline level lying on either side of each absorption peak, these images being denoted $Abs_{\lambda_{b,1}}$ and $Abs_{\lambda_{b,2}}$.

Figure 3C:
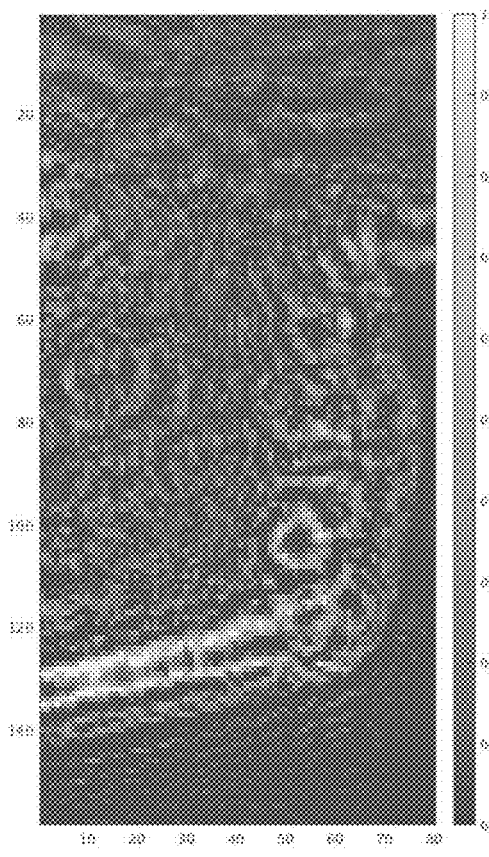
FIG. 3C is an image of the absorbance of a second sample at a wavenumber of 1081 cm$^{-1}$ (i.e. $\lambda$=9.2 μm).
Figure 3D:
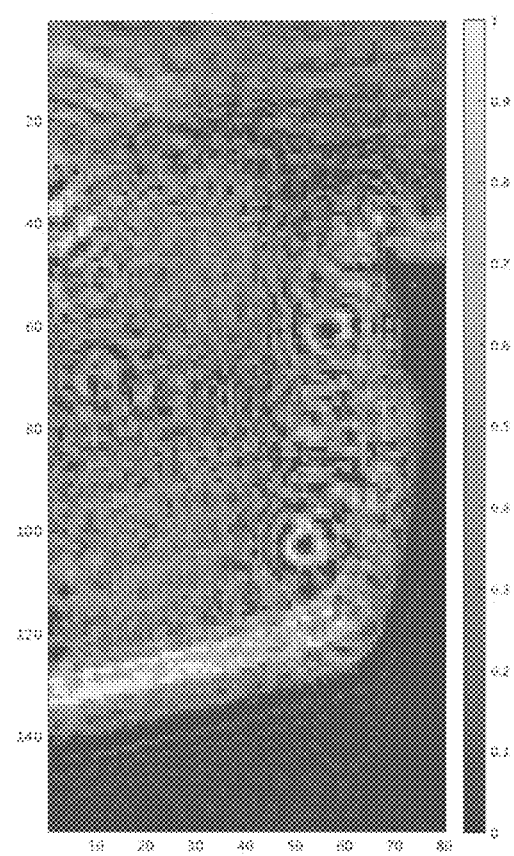
FIG. 3D is an image of the absorbance of the second sample at a wavenumber of 1654 cm$^{-1}$ (i.e. $\lambda$=6 μm).

FIGS. 3C and 3D show an image of absorbance at the wavelengths 1081 cm$^{-1}$ and 1654 cm$^{-1}$.

The absorbance image obtained at a base wavelength was then subtracted from the absorbance image obtained at each absorption wavelength, so as to obtain an image representing an absorbance due to each analyte. In this example, the analytes in question are $PO_2^-$ and an amide group.

The images $I_1$ and $I_2$ of the absorbances due to each analyte, corresponding to $PO_2^-$ and to the amide bond, respectively, are such that:

$$I_1 = Abs_{\lambda_{a,1}} - Abs_{\lambda_{b,1}} \quad (4)$$

$$I_2 = Abs_{\lambda_{a,2}} - Abs_{\lambda_{b,2}} \quad (4')$$

This embodiment amounts to performing steps 100 to 160 described with reference to FIG. 3B, a first time for the wavelengths $\lambda_{a,1}$ and $\lambda_{b,1}$, and a second time for the wavelengths $\lambda_{a,2}$ and $\lambda_{b,2}$.

A ratio $$\frac{I_1}{I_2}$$

between two images $I_1$ and $I_2$ may then be calculated, so as to obtain a map of the nuclear volume/cytoplasmic volume ratio. Depending on the ratio $$\frac{I_1(x,y)}{I_2(x,y)},$$

regions of interest corresponding to cancerous regions are defined in the sample.

As shown by the preceding examples, the invention allows, without labeling, regions of interest of a sample, liable to have a pathological character, to be defined. The lensless imaging configuration allows a large field of observation to be addressed.

The invention claimed is:

1. A device for observing a biological sample, comprising:
   a light source, configured to emit an incident light beam at an emission wavelength comprised between 1 μm and 20 μm;
   an image sensor, comprising pixels, the pixels of the image sensor defining a detection plane;
   a holder, configured to hold the biological sample so that the biological sample is placed between the light source and the image sensor, at a distance from the detection plane smaller than 1 mm,
   wherein
      the light source is further configured to illuminate an area of the biological sample larger than 1 mm$^2$,
      no image-forming optics are placed between the biological sample and the image sensor, and the image sensor is configured to acquire an image corresponding to an area of the biological sample larger than 1 mm$^2$, the acquired image being representative of an absorption of the incident light beam, by the biological sample, at the emission wavelength; and a processing unit, configured to determine a map of an amount of an analyte in the biological sample, on the basis of the image acquired by the image sensor at the emission wavelength, the analyte absorbing light at the emission wavelength.

2. The device according to claim 1, wherein the processing unit is further configured to:

compare the acquired image at the emission wavelength, with a background image at the emission wavelength, so as to obtain an image of the absorbance of the sample at the emission wavelength, the background image at the emission wavelength being an image acquired by the image sensor, at the emission wavelength, with no sample between the image sensor and the light source, and determine the map of the amount of the analyte in the biological sample using the image of the absorbance at the emission wavelength.

3. The device according to claim 2, wherein:

the light source is further configured to illuminate the biological sample at a base wavelength, at which absorption of the analyte is lower than absorption of the analyte at the emission wavelength, the base wavelength being comprised between 1 μm and 20 μm, the image sensor is further configured to acquire a base image of the biological sample at the base wavelength, and the processing unit is further configured to:

compare the base image with a background image at the base wavelength, so as to obtain an image of the absorbance of the biological sample at the base wavelength, the background image at the base wavelength being an image acquired by the image sensor, at the base wavelength, with no sample between the image sensor and the light source, and subtract the absorbance image of the biological sample at the base wavelength from the absorbance image at the emission wavelength so as to obtain an image of absorbance due to the analyte.

4. The device according to claim 3, wherein the light source comprises a first laser configured to emit the incident light beam at the emission wavelength and a second laser configured to emit an incident light beam at the base wavelength.

5. The device according to claim 1, wherein the holder comprises at least one of: silicon, and/or germanium, and/or calcium fluoride, and/or barium fluoride.

6. The device according to claim 1, wherein the holder comprises a thin layer comprising germanium and/or zinc sulfide, the thin layer acting as an anti-reflective coating.

7. The device according to claim 1, wherein the image sensor is formed from a matrix-array of bolometers.

8. The device according to claim 1, wherein the emission wavelength is comprised between 1 μm and 3 μm.

9. The device according to claim 1, wherein the emission wavelength is comprised between 3 μm and 5 μm.

10. The device according to claim 1, wherein the emission wavelength is comprised between 8 μm and 20 μm.

* * * * *